United States Patent

[19]

Hamanaka

[11] 4,359,472

[45] Nov. 16, 1982

[54] BIS-HYDROXYMETHYL CARBONATE BRIDGED ANTIBACTERIAL AGENTS

[75] Inventor: Ernest S. Hamanaka, Groton, Conn.

[73] Assignee: Pfizer Inc., New York, N.Y.

[21] Appl. No.: 334,017

[22] Filed: Dec. 22, 1981

[51] Int. Cl.[3] .................... A61K 31/43; C07D 499/32
[52] U.S. Cl. ................................ 424/271; 260/239.1; 260/245.2 R
[58] Field of Search ................ 260/239.1, 245.2 R; 424/271

[56] References Cited

U.S. PATENT DOCUMENTS

| | | | |
|---|---|---|---|
| 2,985,648 | 5/1961 | Doyle et al. | 260/239.1 |
| 3,192,198 | 6/1965 | Naylor et al. | 260/239.1 |
| 3,520,876 | 7/1970 | Alburn et al. | 260/239.2 |
| 3,928,595 | 12/1975 | Dahlen et al. | 424/271 |
| 4,053,360 | 10/1977 | Bouzard | 195/29 |
| 4,234,579 | 11/1980 | Barth | 424/246 |
| 4,244,951 | 1/1981 | Bigham | 424/250 |

FOREIGN PATENT DOCUMENTS

2044255 10/1980 United Kingdom .

Primary Examiner—Natalie Trousof
Assistant Examiner—Vera C. Clarke

Attorney, Agent, or Firm—Charles J. Knuth; Albert E. Frost; Paul D. Thomas

[57] ABSTRACT

Antibacterial agents in which a penicillin and a beta-lactamase inhibitor are linked by means of a bis-hydroxymethyl carbonate bridge are of the formula:

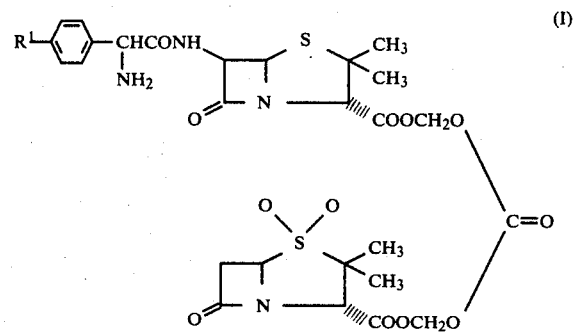

and pharmaceutically acceptable acid addition salts thereof, wherein $R^1$ is hydrogen, hydroxy, certain acyloxy or certain alkoxycarbonyloxy groups, a method for their use, pharmaceutical compositions thereof, and intermediates useful in their production.

19 Claims, No Drawings

BIS-HYDROXYMETHYL CARBONATE BRIDGED ANTIBACTERIAL AGENTS

BACKGROUND OF THE INVENTION

1. Field of the Invention

The invention relates to new chemical compounds which are of value as antibacterial agents. More particularly, it relates to novel bis esters of hydroxymethyl carbonate, $HOCH_2OCOOCH_2OH$, in which one hydroxy group is esterified with the carboxy group of penicillanic acid 1,1-dioxide and the other hydroxy group is esterified with the carboxy group of an alpha-aminopenicillin.

2. Description of the Prior Art

Penicillanic acid 1,1-dioxide (sulbactam) is known from U.S. Pat. No. 4,234,579 to be an effective beta-lactamase inhibitor and antibacterial agent.

In U.S. Pat. No. 4,244,951 and British Patent Application No. 2,044,255 bis esters of the formula:

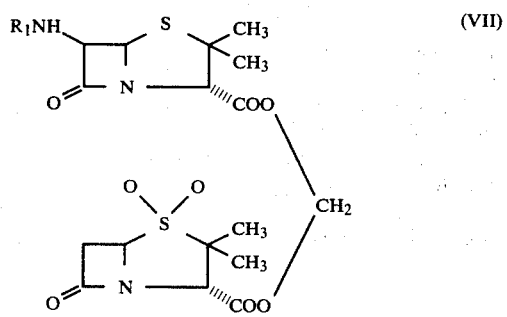

(VII)

are disclosed in which sulbactam is coupled to known antibacterial penicillins via methanediol. In the above formula $R_1$ represents certain acyl groups of known antibacterial penicillins e.g., 2-amino-2-phenylacetyl or 2-amino-2-(p-hydroxyphenyl)acetyl.

In copending application Ser. No. 300,421, filed Sept. 9, 1981 and assigned to the same assignee, compounds of formula (VII) are disclosed wherein $R_1$ is:

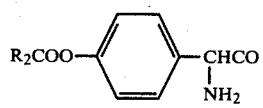

and $R_2$ is certain alkyl or alkoxy groups.

In U.S. Pat. No. 3,928,595 antibacterial compounds are disclosed in which two penicillin or two cephalosporin molecules are bridged via a carbonate ester. These compounds are of the formula:

where $R_4$ is H, $CH_3$ or $C_2H_5$ and $R_3$ is the residue of a penicillin or cephalosporin.

Ampicillin, 6-[D-(2-amino-2-phenylacetamido)]-penicillanic acid is disclosed in U.S. Pat. No. 2,985,648. Amoxicillin, 6-[D-(2-amino-2-[p-hydroxyphenyl)-acetamido)]penicillanic acid is known from U.S. Pat. No. 3,192,198 and U.S. Pat. No. Re. 28,744. p-acyl derivatives of amoxicillin are disclosed in U.S. Pat. No. 2,985,648, U.S. Pat. No. 3,520,876 and U.S. Pat. No. 4,053,360.

SUMMARY OF THE INVENTION

The present invention provides antibacterial compounds of the formula (I) which are efficiently absorbed from the gastrointestinal tract of mammals and after absorption are rapidly transformed into the component alpha-aminobenzylpenicillin (e..g ampicillin or amoxicillin) and penicillanic acid 1,1-dioxide (sulbactam). Said invention compounds are of the formula:

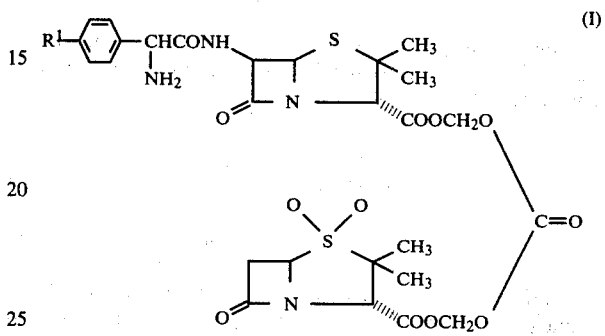

(I)

or a pharmaceutically acceptable acid addition salt thereof, wherein $R^1$ is hydrogen, hydroxy, formyloxy, alkanoyloxy having from two to seven carbon atoms, alkoxycarbonyloxy having from two to seven carbon atoms or $R^2C_6H_4COO$ where $R^2$ is hydrogen, alkyl having from one to four carbon atoms, alkoxy having from one to four carbon atoms, F, Cl, Br, I or CN.

Particularly preferred values for $R^1$ include hydrogen, hydroxy, acetoxy, pivaloyloxy or isobutyryloxy.

The invention also provides valuable intermediates of the formula (II):

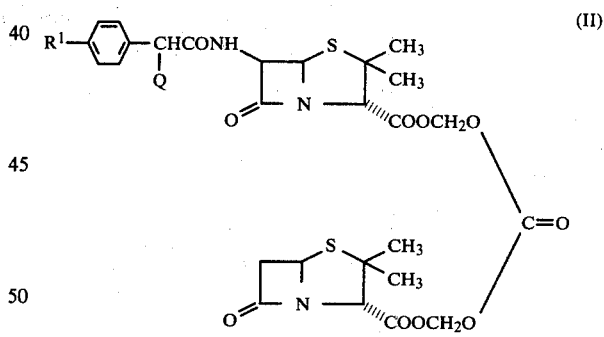

(II)

wherein $R^1$ is as defined above for compound (I) and Q is a group readily convertible to amino, preferably azido, benzyloxycarbonylamino, 4-nitrobenzyloxycarbonylamino or 1-methyl-2-methoxycarbonylvinylamino.

The invention further provides valuable intermediates of the formulae:

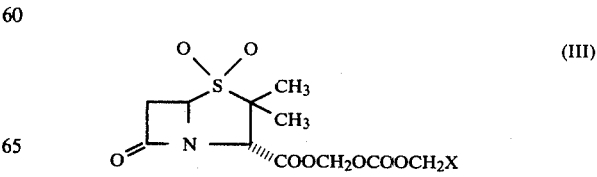

(III)

and

-continued

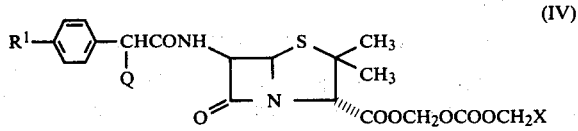

wherein R¹ is as defined above, X is a good leaving group, preferably Cl, Br or I and Q is as defined above for compounds of formula (II).

DETAILED DESCRIPTION OF THE INVENTION

This invention relates to derivatives of penicillanic acid which is represented by the following structural formula:

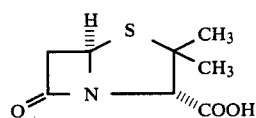

In derivatives of penicillanic acid, broken line attachment ('''') of a substituent to the bicyclic nucleus indicates that the substituent is below the plane of the nucleus. Such a substituent is said to be in the alpha-configuration. Conversely, broad line attachment ( ━ ) of a substituent to the bicyclic nucleus indicates that the substituent is above the plane of the nucleus. This latter configuration is referred to as the beta-configuration. As used herein a solid line attachment (—) of a substituent to the bicylic nucleus indicates that the substituent can be in either the alpha-configuration or the beta-configuration.

Compounds of the invention of the formula (I)–(IV) are named as diesters of carbonic acid. For example, the compound of formula (I) where R¹ is hydrogen is designated as 6-(2-amino-2-phenylacetamido)penicillanoyloxymethyl 1,1-dioxopenicillanoyloxymethyl carbonate; the compound (II) where R¹ is hydroxy and Q is azido is designated as 6-[2-azido-2-(p-hydroxyphenyl)acetamido]penicillanoyloxymethyl 1,1-dioxopenicillanoyloxymethyl carbonate; and the compound of formula (III) where X is iodo is designated as iodomethyl 1,1-dioxopenicillanoyloxymethyl carbonate.

Additionally, throughout this specification, whenever reference is made to compound of formula (I), (II) or (IV), if not already so indicated, it is understood that this refers to a compound in which the substituent:

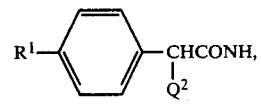

wherein Q² is amino or Q and R¹ and Q are as defined above, has the D-configuration.

The compounds of formula (I) can be prepared by many of the methods known in the art for synthesis of esters. However, the preferred general method involves salt formation by condensation of a carboxylate salt with a halomethyl ester. Two preferred such methods are outlined below.

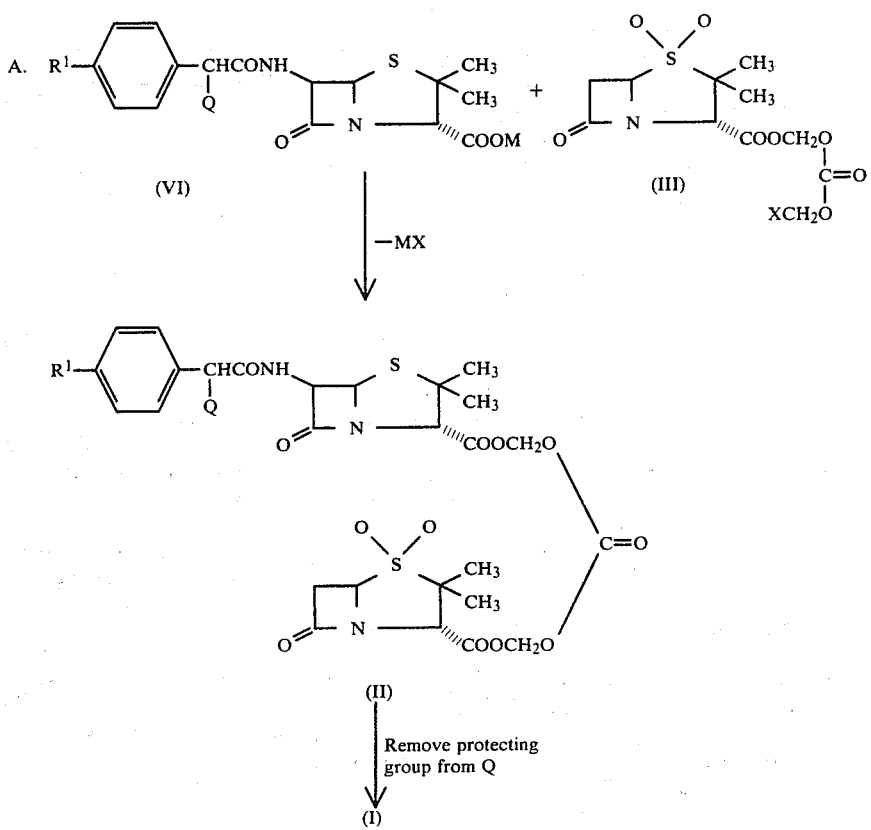

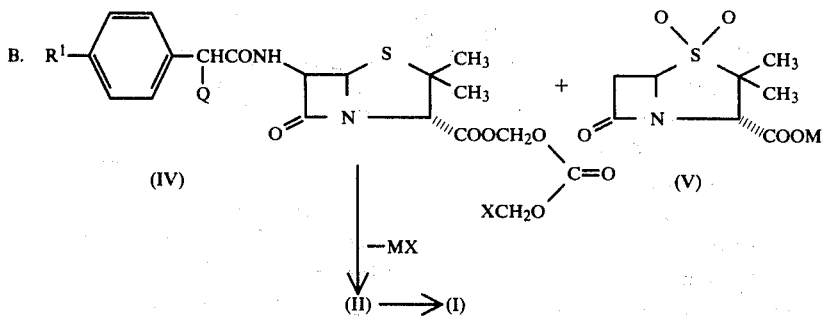

In the above formulae, $R^1$ and $Q$ are as defined above, M is a carboxylate salt forming cation, preferably Na, K or $N(C_4H_9)_4$ cations and X is a good leaving group, preferably Cl, Br or I.

The group $R^1$ in the above intermediates of formulae (IV) and (VI) and products (II) and (I) includes those compounds wherein $R^1$ is acyloxy and alkoxycarbonyloxy as defined above. The carboxylic acid precursors of such intermediates (VI) can be prepared e.g., by methods described in U.S. 4,053,360 by acylation of 6-aminopenicillanic acid with the appropriate acid of the formula:

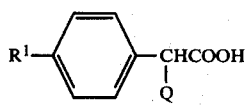

where $R^1$ and Q are as defined above, or an activated derivative thereof, e.g. the acid chloride or mixed anhydride formed with ethyl chloroformate. In the resulting invention compounds (I) and (II) obtained by the above reactions, $R^1$ has the same value as the starting material of formula (VI).

Alternatively, the starting material of formula (IV) or (VI) can be one in which $R^1$ is hydroxy and the resulting intermediate of formula (II) is subsequently acylated or alkoxycarbonylated to form the corresponding compound of formula (II) wherein $R^1$ is alkylcarbonyloxy, alkoxycarbonyloxy or $R^2C_6H_4COD$ as defined above.

The acylation or alkoxycarbonylation of the intermediate of formula (II) wherein $R^1$ is hydroxy and Q is as previously defined can be carried out e.g., by reacting said compound of formula (II) with the appropriate acid chloride or acid anhydride. The reaction is ordinarily carried out in the presence of a reaction-inert solvent system. In a typical procedure, from 0.5 to 2.0 molar equivalents, and preferably about 1 molar equivalent, of the appropriate acid chloride or acid anhydride is contacted with the starting compound of formula (II) wherein $R^1$ is hydroxy, in a reaction-inert solvent, in the presence of a tertiary amine, at a temperature in the range from $-10°$ to $30°$ C. Reaction-inert solvents which can be used in this acylation are: chlorinated hydrocarbons, such as chloroform and dichloromethane; ethers, such as diethyl ether and tetrahydrofuran; low molecular weight esters, such as ethyl acetate and butyl acetate; low molecular weight aliphatic ketones, such as acetone and methyl ethyl ketone; tertiary amides, such as N,N-dimethylformamide and N-methylpyrrolidone; acetonitrile; and mixtures thereof. The tertiary amine is normally used in an amount equivalent to the starting acid chloride or acid anhydride, and typical tertiary amines which can be used are triethylamine, tributylamine, diisopropylethylamine, pyridine and 4-dimethylaminopyridine.

In each of the reaction sequences designated as A and B, above, to form the amino-protected products of formula (II), the respective carboxylate salt and, e.g., halomethyl ester are contacted in approximately equimolar amounts in the presence of a polar organic solvent at a temperature of from about 0° to 80° C. and preferably from 25° to 50° C. While at least equimolar amounts of reactants are ordinarily employed, an excess of the carboxylate salt, up to a ten-fold molar excess, is preferred. A wide variety of solvents can be used for this reaction, however, it is usually advantageous to use a relatively polar organic solvent to minimize the reaction time. Typical solvents which can be employed include N,N-dimethylformamide, N,N-dimethylacetamide, N-methylpyrrolidone, dimethylsulfoxide, ethyl acetate, dichloromethane, chloroform, acetone and hexamethylphosphoric triamide. The time required for the reaction to reach substantial completion varies according to a number of factors, such as the mixture of the reactants, the reaction temperature and solvent. However, at about 25° C. reaction times of from about 10 minutes to about 24 hours are commonly employed.

The desired amino-protected compound of formula (II) is then isolated by methods well known to those of skill in the art. For example, the reaction mixture is taken up in a water immiscible solvent, e.g. ethyl acetate, chloroform or methylene dichloride, washed with water, brine and dried. Evaporation of solvent provides the intermediate of formula (II) which can be purified, if desired, e.g. by chromatography on silica gel.

The removal of the amino-protecting group from the intermediate (II) is carried out by methods well known in the art, see, e.g. Gross et al. in "The Peptides, Analysis, Synthesis, Biology", Academic Press, New York, N.Y., Vol. 3, 1981, but due regard must be given to the lability of the beta-lactam ring and the ester linkages. For example, when Q is 1-methyl-2-methoxycarbonylvinylamino, the protecting group (1-methyl-2-methoxycarbonylvinyl) can be removed simply by treating the compound of formula (II) with one equivalent of a strong aqueous acid, e.g. hydrochloric acid, in a reaction inert solvent, at a temperature in the range of from $-10°$ to $30°$ C. In a typical procedure, the compound of formula (II) is treated with one equivalent of hydrochloric acid in aqueous acetone. The reaction is usually complete within a short time, e.g. within one hour. Then the acetone is removed by evaporation in vacuo, and the methylacetoacetate by-product is removed by extraction with ether. Finally, the compound of formula (I) is recovered by lyophilization as its hydrochloride salt.

Compounds of formula (II) wherein Q is azido, benzyloxycarbonylamino or 4-nitrobenzyloxycarbonylamino can be converted to the corresponding amino compound of formula (I) by subjecting the compound (II) to conditions commonly employed for catalytic hydrogenolysis. The compound of formula (II) is stirred or shaken under an atmosphere of hydrogen, or hydrogen, optionally mixed with an inert diluent such as nitrogen or argon, in the presence of a catalytic amount of a hydrogenolysis catalyst. Convenient solvents for this hydrogenolysis are lower-alkanols, such as methanol and isopropanol; ethers, such as tetrahydrofuran and dioxan; low molecular weight esters, such as ethyl acetate and butyl acetate; chlorinated hydrocarbons, such as dichloromethane and chloroform; water; and mixtures of these solvents. However, it is usual to choose conditions under which the starting material is soluble. The hydrogenolysis is usually carried out at a temperature in the range from 0° to 60° C. and at a pressure in the range from 1 to 10 atmospheres, preferably about 3–4 atmospheres. The catalysts used in this hydrogenolysis reaction are the type of agents known in the art for this kind of transformation, and typical examples are the noble metals, such as nickel, palladium, platinum and rhodium. The catalyst is usually used in an amount from 0.5 to 5.0, and preferably about 1.0, times the weight of the compound of formula (II). It is often convenient to suspend the catalyst on an inert support; a particularly convenient catalyst is palladium suspended on an inert support such as carbon.

The compounds of the formula (I) will form acid addition salts, and these acid addition salts are considered to be within the scope and purview of this invention. Said acid addition salts are prepared by standard methods for penicillin compounds, for example by combining a solution of the compound of formula (I) in a suitable solvent (e.g. water, ethyl acetate, acetone, methanol, ethanol or butanol) with a solution containing a stoichiometric equivalent of the appropriate acid. If the salt precipitates, it is recovered by filtration. Alternatively, it can be recovered by evaporation of the solvent, or, in the case of aqueous solutions, by lyophilization. Of particular value are the sulfate, hydrochloride, hydrobromide, nitrate, phosphate, citrate, tartrate, pamoate, perchlorate, sulfosalicylate, benzenesulfonate, 4-toluenesulfonate and 2-naphthalenesulfonate salts.

The compounds of the formula (I), and the salts thereof, can be purified by conventional methods for penicillin compounds, e.g. recrystallization or chromatography, but due regard must be given to the lability of the beta-lactam ring systems and the ester linkages.

An alternate process for preparation of the antibacterial compounds of formula (I) employs an intermediate of formula:

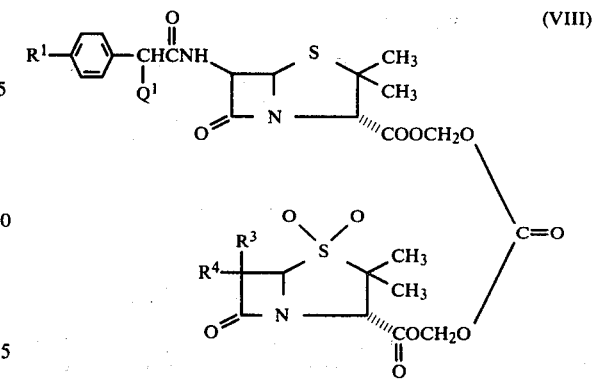

where $R^1$ is as previously defined, $Q^1$ is azido, benzyloxycarbonylamino or p-nitrobenzyloxycarbonylamino, $R^3$ is H, Cl, Br or I and $R^4$ is Cl, Br or I. The intermediate (VIII) upon catalytic hydrogenation, e.g. by the method described above for hydrogenolysis of azido, or benzyloxycarbonylamino compounds of formula (II), is simultaneously hydrogenolyzed at the $Q^1$, $R^3$ and/or $R^4$ substituents to provide the invention compound of formula (I).

The intermediates (VIII) are obtained by methods analogous to those described herein for preparation of intermediates of formula (II), but employing a $R^3,R^4$-substituted 1,1-dioxopenicillanate in place of the corresponding unsubstituted 1,1-dioxopenicillanic acid, its salts or derivatives of formulae (III) or (V).

Methods for preparation of the requisite $R^3,R^4$-disubstituted 1,1-dioxopenicillanic acids and salts thereof are taught in U.S. Pat. No. 4,234,579; British Patent Application No. 2,044,255 and Belgian Pat. No. 882,028.

The intermediates of formula (IV) are obtained, for example, as outlined below:

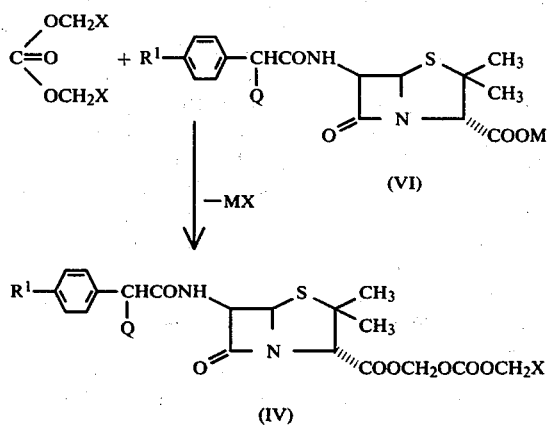

where $R^1$, M, Q and X are as defined above. The reaction is carried out by contacting the starting amino-protected benzylpenicillin salt of formula (VI) with at least an equimolar amount, preferably a molar excess of up to ten-fold, of a bis-halomethyl carbonate in the presence of a reaction inert organic solvent and a temperature of from about −20° to 60° C., preferably from 0° to 30° C. The solvents which can be employed successfully in this reaction include the same polar organic solvents employed above for preparation of intermediates of formula (II).

The intermediate halomethyl 1,1-dioxopenicillanoyloxymethyl carbonates of formula (III) are prepared as described above for the intermediates of formula (IV), but employing a salt of penicillanic acid 1,1-dioxide of formula (V) as starting material in place of the starting penicillin salt of formula (VI).

bis-Chloromethyl carbonate is prepared by photochemical chlorination of dimethyl carbonate by the method of Kling et al., *Compt. rend.*, 170, 111, 234 (1920); *Chem. Abstr.*, 14, 1304 (1920). bis-Bromomethyl carbonate and bis-iodomethylcarbonate are obtained from the bis-chloromethyl compound by reaction with e.g. sodium bromide or potassium iodide by methods well known in the art.

The carboxylate salts of formulae (V) and (VI) are obtained from the corresponding carboxylic acids. A preferred method for providing the salts wherein M is an alkali metal such as sodium or potassium employs the appropriate salt of 2-ethylhexanoic acid as base. Typically, the carboxylic acid of formula (V) or (VI) is dissolved in ethyl acetate, an equimolar amount of sodium or potassium 2-ethylhexanoate is added with stirring and the precipitated salt of formula (V) or (VI) collected by filtration.

The corresponding salts of formula (V) or (VI) where M is tetrabutylammonium can be obtained from the corresponding acid, e.g. by neutralization with aqueous tetrabutylammonium hydroxide in the presence of a water immiscible organic solvent, preferably chloroform. The solvent layer is separated and the product isolated by evaporation of solvent. Alternately, the sodium or potassium salts of formula (V) or (VI) are reacted with an equimolar amount of aqueous tetrabutylammonium hydrogen sulfate in the presence of a water immiscible solvent, the precipitated alkali metal bisulfate salt removed by filtration and the product isolated by evaporation of solvent.

While in the present invention the antibacterial compounds of the formula (I), as defined above, are the preferred compounds wherein a penicillin and a beta-lactamase inhibitor are linked as a bis-ester of hydroxymethyl carbonate, in a broader sense the invention relates to antibacterial compounds of the general formula:

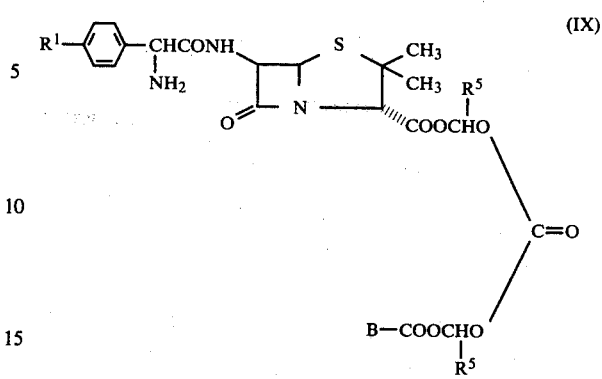

where $R^5$ is hydrogen or alkyl having from one to three carbon atoms, B is the residue of certain beta-lactamase inhibitors and $R^1$ is as defined above.

Examples of beta-lactamase inhibitors, B, include:

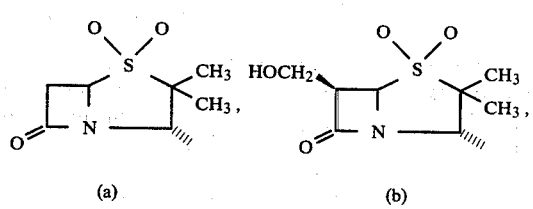

(a)      (b)

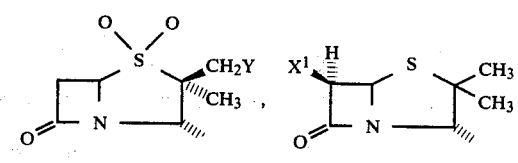

where Y is Cl or $CH_3COO$    where $X^1$ = Cl, Br or I
(c)      (d)

and

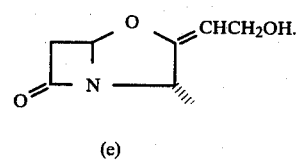

(e)

The preferred compounds of formula (I), those above wherein the beta-lactamase inhibitor residue, B, is 1,1-dioxopenicillanoyl, (a), are prepared, as described above, employing hydrogenolysis methods. Analogous compounds of formula (IX) wherein B is moiety (b), above are similarly obtained. However, certain of the above moieties B are not stable to hydrogenolysis. Thus, preparation of compounds of formula (IX) wherein B is a moiety that is unstable to hydrogenolysis conditions such as (c), (d) or (e), above, requires the use of a protecting group which is removable by mild hydrolysis, for example, as outlined below:

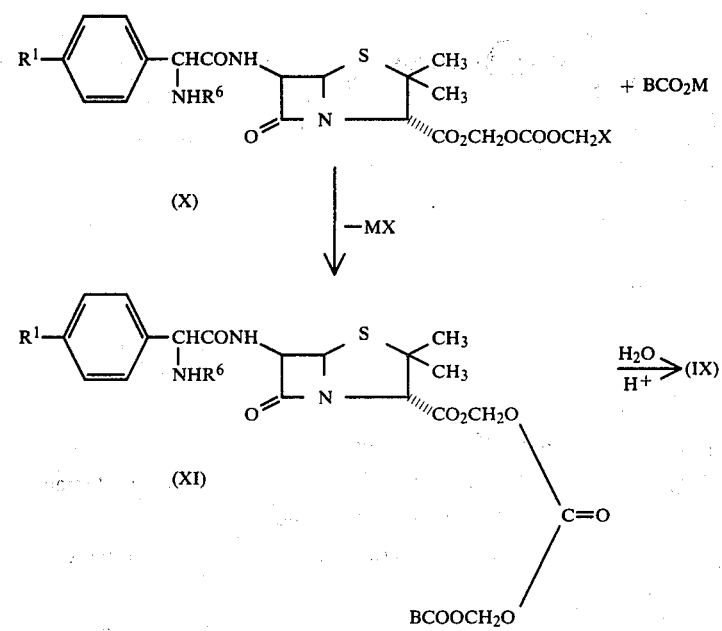

where B, M, $R^1$ and X are as defined above and $R^6$ is an amino protecting group which is removable by mild hydrolysis, e.g., triphenylmethyl or an enamino group such as:

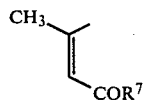

where $R^7$ is alkoxy having from one to three carbon atoms or amino.

Alternately, of course, the compounds of formula (IX) which are not stable to hydrogenolysis conditions can be prepared by the following methods:

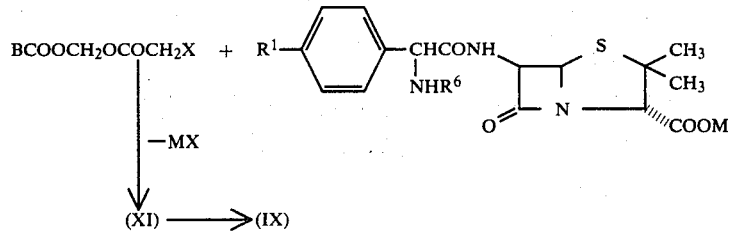

where B, M, $R^1$, X and $R^6$ are as defined above.

When contemplating therapeutic use for a salt of an antibacterial compound of this invention, it is necessary to use a pharmaceutically-acceptable salt; however, salts other than these can be used for a variety of purposes. Such purposes include isolating and purifying particular compounds, and interconverting pharmaceutically-acceptable salts and their non-salt counterparts.

The compounds of formula (I) and pharmaceutically acceptable acid addition salts thereof possess in vivo antibacterial activity in mammals, and this activity can be demonstrated by standard techniques for penicillin compounds. For example, the compound of formula (I) is administered to mice in which acute infections have been established by intraperitoneal inoculation with a standardized culture of a pathogenic bacterium. Infection severity is standardized such that the mice receive one to ten times the $LD_{100}$ ($LD_{100}$: the minimum inoculation required to consistently kill 100 percent of control mice). At the end of the test, the activity of the compound is assessed by counting the number of survivors which have been challenged by the bacterium and also have received the invention compound. The compounds of formula (I) can be administered by both the oral (p.o.) and subcutaneous (s.c.) route.

The in vivo activity of the antibacterial compounds of this invention makes them suitable for the control of bacterial infections in mammals, including man, by both the oral and parenteral modes of administration. The compounds are useful in the control of infections caused by susceptible bacteria in human subjects.

A compound of formula (I) wherein $R^1$ is other than hydrogen breaks down to 6-(2-amino-2-[4-hydroxyphenyl]acetamido)penicillanic acid (amoxicillin) and penicillanic acid 1,1-dioxide (sulbactam) after administration to a mammalian subject by both the oral and parenteral route. Sulbactam then functions as a beta-lactamase inhibitor, and it increases the antibacterial effectiveness of the amoxicillin. Similarly, a compound of formula (I) wherein $R^1$ is hydrogen breaks down to 6-(2-amino-2-phenylacetamido)penicillanic acid (ampicillin) and sulbactam. Thus, th compounds of the formula (I) will find use in the control of bacteria which are susceptible to a 1:1 mixture of amoxicillin and sulbactam or ampicillin and sulbactam, e.g. susceptible strains of *Escherichia coli* and *Staphylococcus aureus.*

In determining whether a particular strain of *Escherichia coli* or *Staphylococcus aureus* is sensitive to a particular therapeutic compound of the invention, the in vivo test described earlier can be used. Alternatively, e.g., the minimum inhibitory concentration (MIC) of a 1:1 mixture of amoxicillin and sulbactam or ampicillin/sulbactam can be measured. The MIC's can be measured by the procedure recommended by the International Collaborative Study on Antibiotic Sensitivity Testing (Ericcson and Sherris, *Acta. Pathologica et Microbiologia Scandinavica,* Supp. 217, Section B: 64–68 [1971]), which employs brain heart infusion (BHI) agar and the inocula replicating device. Overnight growth tubes are diluted 100 fold for use as the standard inoculum (20,000–10,000 cells in approximately 0.002 ml. are placed on the agar surface; 20 ml. of BHI agar/dish). Twelve 2 fold dilutions of the test compound are employed, with initial concentration of the test drug being 200 mcg./ml. Single colonies are disregarded when reading plates after 18 hrs. at 37° C. The susceptibility (MIC) of the test organism is accepted as the lowest concentration of compound capable of producing complete inhibition of growth as judged by the naked eye.

When using an antibacterial compound of this invention, or a salt thereof, in a mammal, particularly man, the compound can be administered alone, or it can be mixed with other antibiotic substances and/or pharmaceutically-acceptable carriers or diluents. Said carrier or diluent is chosen on the basis of the intended mode of administration. For example, when considering the oral mode of administration, an antibacterial compound of this invention can be used in the form of tablets, capsules, lozenges, troches, powders, syrups, elixirs, aqueous solutions and suspensions, and the like, in accordance with standard pharmaceutical practice. The proportional ratio of active ingredient to carrier will naturally depend on the chemical nature, solubility and stability of the active ingredient, as well as the dosage contemplated. In the case of tablets for oral use, carriers which are commonly used include lactose, sodium citrate and salts of phosphoric acid. Various disintegrants such as starch, and lubricating agents, such as magnesium stearate, sodium lauryl sulfate and talc, are commonly used in tablets. For oral administration in capsule form, useful diluents are lactose and high molecular weight polyethylene glycols, e.g. polyethylene glycols having molecular weights of from 2000 to 4000. When aqueous suspensions are required for oral use, the active ingredient is combined with emulsifying and suspending agents. If desired, certain sweetening and/or flavoring agents can be added. For parenteral administration, which includes intramuscular, intraperitoneal, subcutaneous, and intravenous use, sterile solutions of the active ingredient are usually prepared, and the pH of the solutions are suitably adjusted and buffered. For intravenous use, the total concentration of solutes should be controlled to render the preparation isotonic.

As indicated earlier, the antibacterial compounds of this invention are of use in human subjects and the daily dosages to be used will not differ significantly from other, clinically-used, penicillin antibiotics. The prescribing physician will ultimately determine the appropriate dose for a given human subject, and this can be expected to vary according to the age, weight, and response of the individual patient as well as the nature and the severity of the patient's symptoms. The compounds of this invention will normally be used orally at dosages in the range from 20 to about 100 mg. per kilogram of body weight per day, and parenterally at dosages from about 10 to about 100 mg. per kilogram of body weight per day, usually in divided doses. In some instances it may be necessary to use doses outside these ranges.

The following examples and preparations are provided solely for further illustration. Nuclear magnetic resonance spectra (NMR) were measured for solutions in deuterated chloroform ($CDCl_3$) or deuterated dimethyl sulfoxide ($DMSO-d_6$), and peak positions are reported in parts per million downfield from tetramethylsilane. The following abbreviations for peak shapes are used: bs, broad singlet; s, singlet; d, doublet; t, triplet; q, quartet, m, multiplet.

EXAMPLE 1 bis-Iodomethyl Carbonate

To a solution of 10.7 ml. (15.9 g., 0.1 mole) bis(-chloromethyl)carbonate in 400 ml. acetone was added 75 g. (0.5 mole) sodium iodide. The mixture was refluxed for 2 hours under nitrogen, then left overnight at room temperature. The mixture was filtered and the filtrate was concentrated in vacuo. Methylene chloride (500 ml.) was added and the resulting mixture was filtered. The filtrate was concentrated to about 200 ml., 200 ml. of water was added and the aqueous phase was adjusted to pH 7.5. Aqueous sodium thiosulfate solution was added to remove iodine, the organic phase was separated and dried over sodium sulfate. The dried methylene chloride solution was concentrated in vacuo to an oil which darkened on standing. The oily product was treated with a mixture of 35 ml. hexane and 6 ml. diethyl ether at 0° C., the resulting crystals were filtered, washed with hexane and dried, to afford 10.0 g. (29%) of yellowish crystalline product. M.P. 49°–51° C. $^1$H-NMR ($CDCl_3$) ppm (delta): 5.94 singlet; infrared spectrum (Nujol) $cm^{-1}$: 1756, 1775.

EXAMPLE 2

Iodomethyl 6-[D-(2-azido-2-phenylacetamido)]penicillanoyloxymethyl carbonate

To a cooled solution (0° C.) of 2.43 g. (7.1 mmoles) of bis-iodomethyl carbonate in chloroform (16 ml.), a solution of 2.19 g. (3.5 mmole) of tetrabutylammonium 6-[D-(2-azido-2-phenylacetamido)]penicillanate in 10 ml. chloroform was added dropwise. After the addition was completed the reaction mixture was allowed to warm to room temperature and allowed to stand at room temperature overnight. The solvent was removed in vacuo and the residue was chromatographed on silica gel, eluting with 8:1 by volume methylene chloride/ethyl acetate to yield 822 mg. (40%) of product. $^1$H-NMR ($CDCl_3$) ppm (delta): 1.52 (s, 3H), 1.65 (s, 3H), 4.45 (s, 1H), 5.04 (s, 1H), 5.65 (m, 4H), 5.92 (s, 2H), 7.34 (s, 5H); infrared spectrum ($CHCl_3$): 1770 $cm^{-1}$.

EXAMPLE 3

6-[D-(2-azido-2-phenylacetamido)]penicillanoyloxymethyl 1,1-dioxopenicillanoyloxymethyl Carbonate (II, $R^1$=H, Q=$N_3$)

To a solution of 822 mg. (1.4 mmole) iodomethyl 6-[D-(2-azido-2-phenylacetamido)]penicillanoyloxymethyl carbonate in 30 ml. chloroform was added dropwise at room temperature a solution of 1.33 g. (2.8 mmole) tetrabutylammonium 1,1-dioxopenicillanate in 30 ml. chloroform. The reaction mixture was stirred at room temperature overnight, concentrated in vacuo and chromatographed on silica gel. Elution with 9:1 by volume methylene chloride/ethyl acetate gave 0.51 g. of product (52.6% yield). $^1$H-NMR (CDCl$_3$) ppm (delta): 1.4 (s, 3H), 1.5 (s, 3H), 1.6 (s, 3H), 1.64 (s, 3H), 3.42 (d, J=3 Hz, 2H), 4.4 (s, 1H), 4.44 (s, 1H), 4.6 (t, J=3 Hz, 1H), 5.04 (s, 1H), 5.44–6.0 (m, 6H), 7.35 (s, 5H); infrared spectrum (CHCl$_3$): 1775 cm$^{-1}$.

EXAMPLE 3A

When the procedure of Example 2 is carried out with the tetrabutylammonium salt of 6-[D-(2-benzyloxycarbonylamino-2-phenylacetamido)]penicillanate in place of the corresponding azidocillin salt, the product obtained is iodomethyl 6-[D-(2-benzyloxycarbonylamino-2-phenylacetamido)]penicillanoyloxymethyl carbonate. When the latter compound is employed as starting material in the procedure of Example 3, the product obtained is 6-[D-(2-benzyloxycarbonylamino-2-phenylacetamido)]penicillanoyloxymethyl 1,1-dioxopenicillanoyloxymethyl carbonate.

Similarly, starting with the 6-[D-(2-p-nitrobenzyloxycarbonylamino-2-phenylacetamido)]penicillanate salt in the method of Example 2 and carrying the product through the method of Example 3, provides 6-[D-(2-p-nitrobenzyloxycarbonylamino-2-phenylacetamido)]-penicillanoyloxymethyl 1,1-dioxopenicillanoyloxymethyl carbonate.

EXAMPLE 4

6-[D-(2-amino-2-phenylacetamido)]penicillanoyloxymethyl 1,1-dioxopenicillanoyloxymethyl carbonate (I, R$^1$=H)

A solution of 1.49 g. 6-[D-(2-azido-2-phenylacetamido)]penicillanoyloxymethyl 1,1-dioxopenicillanoyloxymethyl carbonate in 40 ml. methylene chloride and 20 ml. isopropanol was hydrogenated at 60 psi (4.2 kg./cm.$^2$) in the presence of 1.5 g. 10% Pd/C for 30 minutes. A further 1.5 g. of catalyst was added and the hydrogenation was continued for another 30 minutes. The catalyst was then filtered off and the filtrate was concentrated to provide a white solid residue. The residue was dissolved in tetrahydrofuran/water (1:1), the resulting solution was cooled to 0° C. and adjusted to pH 2.5 with 0.1 N hydrochloric acid. The tetrahydrofuran was evaporated in vacuo and the resulting aqueous solution was freeze dried to afford 680 mg. (45%) of product as a white solid. $^1$H-NMR (CDCl$_3$+CD$_3$OD) ppm (delta): 1.42 (s, 6H), 1.5 (s, 3H), 1.6 (s, 3H), 3.46 (m, 2H), 4.4 (s, 1H), 4.43 (s, 1H), 4.72 (m, 1H), 5.2 (s, 1H), 5.48 (q, J=4 Hz, 2H), 5.82 (s+q, J=6 Hz, 4H), 7.44 (s, 5H); infrared spectrum (Nujol): 1775 cm$^{-1}$.

When the corresponding benzyloxycarbonylamino compounds provided in Example 3A are employed as starting material in the above procedure, the same title compound is obtained in like manner.

EXAMPLE 5

Chloromethyl 1,1-dioxopenicillanoyloxymethyl carbonate

To a mixture of 1.17 g. (5 mmole) penicillanic acid, 1,1-dioxide, 50 ml. chloroform and 10 ml. water is added 40% aqueous tetrabutylammonium hydroxide with vigorous stirring until a pH of 8.5 is obtained. The chloroform layer is separated and the aqueous phase extracted with fresh chloroform. The combined organic layers are dried and concentrated to a small volume (about 20 ml.).

To a solution of 1.5 g. (10 mmole) bis-chloromethyl carbonate in 15 ml. chloroform at 0° C. is added dropwise the above solution of tetrabutylammonium 1,1-dioxopenicillanate. After the addition is completed, the mixture is allowed to warm to room temperature and stir overnight. The chloroform is evaporated in vacuo and the crude product purified by chromatography on silica gel.

EXAMPLE 6

Iodomethyl 1,1-dioxopenicillanoyloxymethyl carbonate

To a solution of 3.37 g. (10 mmole) chloromethyl 1,1-dioxopenicillanoxymethyl carbonate in 50 ml. acetone is added 7.5 g. (50 mmole) sodium iodide and the mixture is stirred overnight at room temperature. The acetone is evaporated in vacuo, the residue partitioned between water and ethyl acetate. The aqueous phase is separated, the organic phase washed with water, brine, dried, (Na$_2$SO$_4$) and concentrated in vacuo to give the iodomethyl compound which is purified, if desired, by chromatography on silica gel.

When the above procedure is repeated but using dimethylformamide as solvent in place of acetone and sodium bromide in place of sodium iodide, bromomethyl 1,1-dioxopenicillanoyloxymethyl carbonate is obtained.

EXAMPLE 7

6-[D-(2-[1-methyl-2-methoxycarbonylvinylamino]-2-[p-hydroxyphenyl]acetamido)]penicillanoyloxymethyl 1,1-dioxopenicillanoyloxymethylcarbonate (II, R$^1$=OH, Q=NHCH(CH$_3$)=CHCO$_2$CH$_3$]

A. To 300 ml. of dichloromethane is added 41.9 g. of 6-(2-amino-2-[4-hydroxyphenyl]acetamido)penicillanic acid trihydrate and 50 ml. of water, and then the pH is adjusted to 8.5 using 40% aqueous tetrabutylammonium hydroxide. Three layers are obtained. The upper layer is removed, saturated with sodium sulfate and then it is extracted with dichloromethane. The extracts are combined with the middle layer and the lower layer, and the resulting mixture is evaporated in vacuo to give an oil which crystallized on triturating with acetone. This afforded 44.6 g. of tetrabutylammonium 6-(2-amino-2-[4-hydroxyphenyl]acetamido)penicillanate.

The above salt is added to 150 ml. of methyl acetoacetate and the suspension is heated at ca. 65° C. until a clear solution is obtained (8 minutes). The mixture is allowed to cool, and the solid recovered by filtration. The solid is washed with methyl acetoacetate, followed by diethyl ether, to give 49.25 g. of tetrabutylammonium 6-(2-[1-methyl-2-methoxycarbonylvinylamino]-2-[4-hydroxyphenyl]acetamido)penicillanate.

B. A mixture of 7.04 g. (0.01 mole) of the tetrabutylammonium salt of amoxicillin enamine obtained in Part A, 4.28 g. (0.01 mole) iodomethyl 1,1-dioxopenicillanoyloxymethyl carbonate and 65 ml. chloroform is stirred at room temperature for eight hours. The mixture is diluted with 500 ml. ethyl acetate, washed with brine, water, brine again and dried (Na$_2$SO$_4$). The solvent is evaporated in vacuo, the residual product is dissolved in a minimal amount of ethyl acetate and purified by chromatography on silica gel.

EXAMPLE 8

6-[D-(2-Amino-2-[p-hydroxyphenyl]acetamido)]-penicillanoyloxymethyl 1,1-dioxopenicillanoyloxymethyl carbonate hydrochloride (I, $R^1$=OH)

To 2.5 g. 6-[D-(2-[1-methyl-2-methoxycarbonyl-vinylamino]-2-[p-hydroxyphenyl]acetamido)]penicillanoyloxymethyl 1,1-dioxopenicillanoyloxymethyl carbonate dissolved in 60 ml. acetone is added 33 ml. 0.1 N hydrochloric acid and the mixture is stirred for 20 minutes at room temperature. The acetone is evaporated in vacuo, the aqueous residue extracted with ethyl ether, then with ethyl acetate. The aqueous layer is then freeze dried to afford the title hydrochloride salt.

EXAMPLE 9

6-[D-(2-Amino-2-phenylacetamido)]penicillanoyloxymethyl 1,1-dioxopenicillanoyloxymethyl carbonate hydrochloride (I, $R^1$=H)

To 300 ml. chloroform is added 40.3 g. ampicillin trihydrate and 50 ml. water. The pH is adjusted to 8.5 with 40% aqueous tetrabutylammonium hydroxide, and the tetrabutylammonium salt isolated and reacted with methyl acetoacetate by the method of Example 7, Part A but using chloroform as solvent in place of dichloromethane. The resulting tetrabutylammonium 6-[D-(2-[1-methyl-2-methoxycarbonylvinylamino]-2-phenylacetamido)]penicillanate (obtained in 52% yield) is reacted with iodomethyl 1,1-dioxopenicillanoyloxymethyl carbonate by the method of Example 7, Part B to provide 6-[D-(2-[1-methyl-2-methoxycarbonyl-vinylamino]-2-phenylacetamido)]penicillanoyloxymethyl 1,1-dioxopenicillanoyloxymethyl carbonate. Removal of the enamine protecting group with aqueous hydrochloric acid in acetone by the method of Example 8 provides the title compound.

The compounds of the formula below are obtained in like manner:

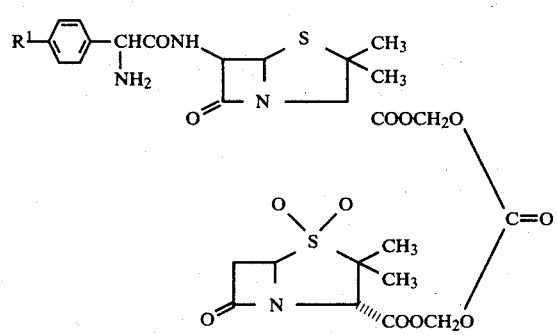

where $R^1$ is:
CH₃COO
C₂H₅COO
(CH₃)₂CHCOO
CH₃(CH₂)₃COO
CH₃(CH₂)₅COO
CH₃OCOO
(CH₃)₂CHOCOO
(CH₃)₃COCOO
CH₃(CH₂)₅OCOO
C₆H₅COO
4-FC₆H₄COO
2-ClC₆H₄COO
3-BrC₆H₄COO
4-CNC₆H₄COO
4-CH₃C₆H₄COO
3-(CH₃)₂CHC₆H₄COO
4-(CH₃)₃CC₆H₄COO
3-CH₃OC₆H₄COO
4-C₂H₅OC₆H₄COO
2-n-C₃H₇OC₆H₄COO
3-(CH₃)₂CHCH₂OC₆H₄COO
4-n-C₄H₉OC₆H₄COO
HCOO.

EXAMPLE 10

6-[D-(2-Amino-2-[p-acetoxyphenyl]acetamido)]penicillanoyloxymethyl 1,1-dioxopenicillanoyloxymethyl carbonate hydrochloride (I, $R^1$=CH₃COO)

A. 6-[D-(2-[1-methyl-2-methoxycarbonyl-vinylamino]-2-[p-acetoxyphenyl]acetamido)]penicillanoyloxymethyl 1,1-dioxopenicillanoyloxymethyl carbonate:

6-[D-(2-[1-methyl-2-methoxycarbonylvinylamino]-2-[p-hydroxyphenyl]acetamido)]penicillanoyloxymethyl 1,1-dioxopenicillanoyloxymethyl carbonate 2.34 g. (3 mmole), prepared by the method of Example 7, and 0.366 g. (3 mmole) 4-dimethylaminopyridine are dissolved in 30 ml. dichloromethane and 0.28 ml. (3 mmole) acetic anhydride is added. The solution is stirred for 30 minutes, diluted to 100 ml. with dichloromethane, washed with water and brine, then dried (Na₂SO₄). Evaporation of solvent in vacuo affords the title compound.

B. To 1.9 g. of the product obtained in Part A, above, dissolved in 50 ml. acetone is added 23 ml. 0.1 N hydrochloric acid. The resulting mixture is stirred for 25 minutes at room temperature and the acetone evaporated in vacuo. The aqueous phase is washed with ethyl ether, clarified by filtration and freeze dried to yield the title compound.

EXAMPLE 11

6-[D-(2-Amino-2-[p-pivaloyloxyphenyl]acetamido)]-penicillanoyloxymethyl 1,1-dioxopenicillanoyloxymethyl carbonate hydrochloride [I, $R^1$=(CH₃)₃CCOO]

The title compound is obtained by repeating the procedure of Example 10, but using 0.33 g. (3 mmole) of pivaloyl chloride in place of the acetic anhydride in Part A. The enamine protecting group is removed from the resulting p-pivaloyloxyphenyl ester with aqueous hydrochloric acid in acetone and the product isolated as described in Part B of Example 10.

Use of isobutyryl chloride or isobutyric anhydride in the above procedure affords the corresponding compound of formula (I) where $R^1$ is (CH₃)₂CHCOO.

Similarly, use of ethyl chloroformate as the acylating agent provides the corresponding compound of formula (I) where $R^1$ is CH₃CH₂OCOO and use of formic-acetic anhydride as acylating agent yields (I) where $R^1$ is formyloxy.

EXAMPLE 12

When the procedure of Example 11 is repeated, but employing the appropriate acid anhydride, acid chloride, acid bromide or chloroformate ester as acylating agent, the following compounds wherein Q is NHC(CH₃)=CHCO₂CH₃ are obtained and hydrolyzed to the corresponding compounds of the formula wherein Q is NH₂.

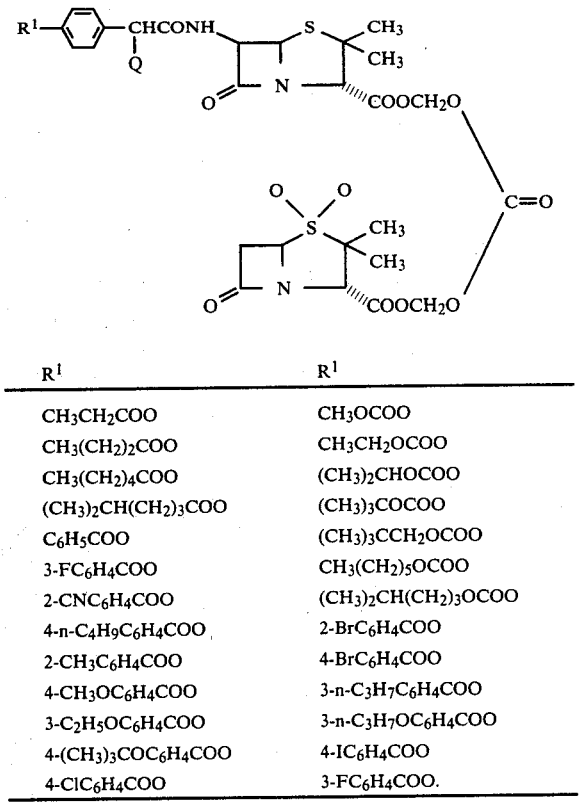

| R¹ | R¹ |
|---|---|
| CH₃CH₂COO | CH₃OCOO |
| CH₃(CH₂)₂COO | CH₃CH₂OCOO |
| CH₃(CH₂)₄COO | (CH₃)₂CHOCOO |
| (CH₃)₂CH(CH₂)₃COO | (CH₃)₃COCOO |
| C₆H₅COO | (CH₃)₃CCH₂OCOO |
| 3-FC₆H₄COO | CH₃(CH₂)₅OCOO |
| 2-CNC₆H₄COO | (CH₃)₂CH(CH₂)₃OCOO |
| 4-n-C₄H₉C₆H₄COO | 2-BrC₆H₄COO |
| 2-CH₃C₆H₄COO | 4-BrC₆H₄COO |
| 4-CH₃OC₆H₄COO | 3-n-C₃H₇C₆H₄COO |
| 3-C₂H₅OC₆H₄COO | 3-n-C₃H₇OC₆H₄COO |
| 4-(CH₃)₃COC₆H₄COO | 4-IC₆H₄COO |
| 4-ClC₆H₄COO | 3-FC₆H₄COO. |

EXAMPLE 13

6-[D-(2-[Benzyloxycarbonylamino]-2-[p-hydroxyphenyl]acetamido)]penicillanoyloxymethyl 1,1-dioxopenicillanoyloxymethyl carbonate (II, R¹=OH, Q=NHCbz)

To 7.40 g. (0.010 mole) tetrabutylammonium 6-[D-(2-[benzyloxycarbonylamino]-2-[p-hydroxyphenyl]acetamido)]penicillanate and 3.81 g. (0.010 mole) bromomethyl 1,1-dioxopenicillanoyloxymethyl carbonate is added 50 ml. dimethylformamide and the mixture is stirred for four hours. Ethyl acetate (500 ml.) is added and the mixture washed in turn with brine, water, brine again and dried over anhydrous sodium sulfate. Evaporation of solvent in vacuo affords the crude product which can be purified by chromatography on silica gel, if desired.

Reaction of compounds of the formula (IV) with amino-protected penicillin salts of the formula (VI) by the above procedure affords products of formula (II) in like manner, where R¹, Q, M and X are as defined below.

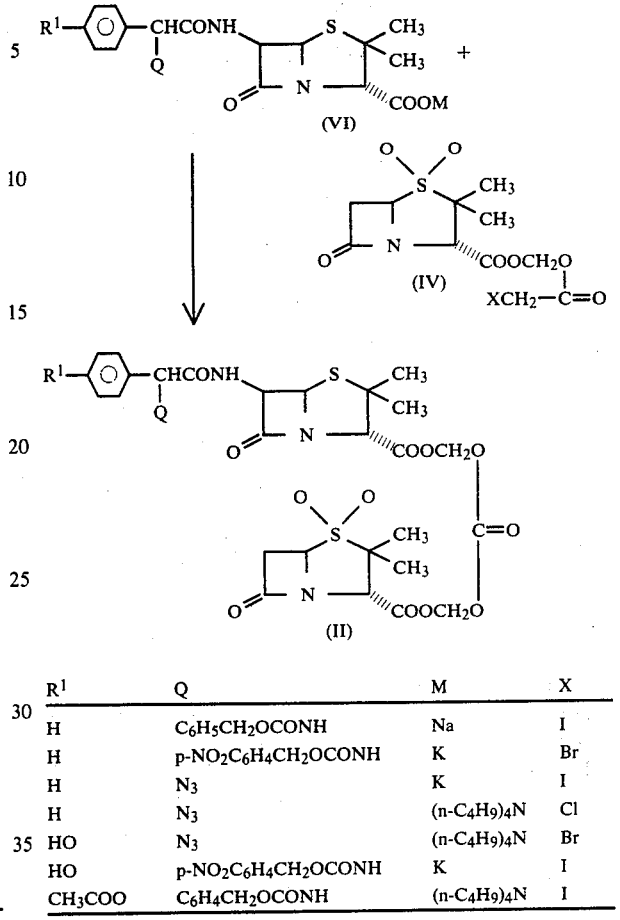

| R¹ | Q | M | X |
|---|---|---|---|
| H | C₆H₅CH₂OCONH | Na | I |
| H | p-NO₂C₆H₄CH₂OCONH | K | Br |
| H | N₃ | K | I |
| H | N₃ | (n-C₄H₉)₄N | Cl |
| HO | N₃ | (n-C₄H₉)₄N | Br |
| HO | p-NO₂C₆H₄CH₂OCONH | K | I |
| CH₃COO | C₆H₄CH₂OCONH | (n-C₄H₉)₄N | I |

EXAMPLE 14

6-[D-(2-Amino-2-[p-hydroxyphenyl)acetamido)]-penicillanoyloxymethyl]-1,1-dioxopenicillanoyloxymethyl carbonate (I, R¹=OH)

A mixture of 2.0 g. 6-[D-(2-[benzyloxycarbonylamino]-2-[p-hydroxyphenyl]acetamido)]penicillanoyloxymethyl 1,1-dioxopenicillanoyloxymethyl carbonate, 50 ml. dichloromethane, 50 ml. isopropanol and 2.0 g. 10% palladium-on-carbon is hydrogenated at 3-4 atmospheres (3.5-4.0 kg./cm.²) until hydrogen uptake ceases. An additional 2 g. of catalyst is added and hydrogenation continued for 30 minutes. The catalyst is removed by filtration and the filtrate evaporated in vacuo to afford the product which can be purified, if desired, by chromatography on Sephadex LH 20*.

*A registered trademark of Pharmacia Fine Chemicals, Piscataway, N.J.

EXAMPLE 15

The remaining compounds of formula (II) provided in Example 13 are converted to the corresponding alpha-mino compound of formula (I) by the method of the preceding Example:

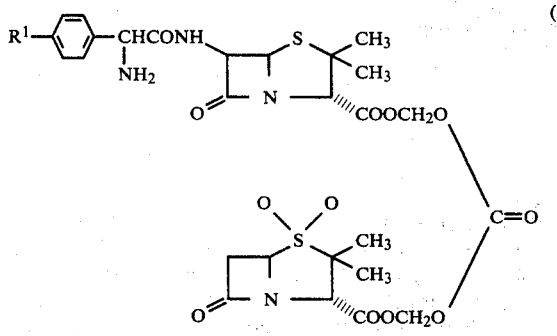

(I)

where R[1] is as defined for the starting material of formula (II).

PREPARATION A bis-Chloromethyl Carbonate

The method is essentially that of Kling et al., *Compt. rend.* 170, 111–113, 234–236 (1920); *Chem. Abstr.*, 14, 1304 (1920).

A solution of 59 ml. dimethyl carbonate in 120 ml. carbon tetrachloride is cooled in an ice bath. Chlorine gas is bubbled into the solution while irradiating with a sun lamp until most of the starting material is reacted. The excess chlorine is displaced by nitrogen, the solvent evaporated and the residue was distilled through a short column with fractionating head at 50 mm. pressure. The desired product boils at 95°–100° C./50 mm. Yield, 68 g.

PREPARATION B

Tetrabutylammonium 6-(2-Benzyloxycarbonylamino-2-[4-hydroxyphenyl]acetamido)penicillanate To a rapidly stirred mixture of 1.0 g. of 6-(2-benzyloxycarbonylamino-2-[4-hydroxyphenyl]acetamido)-penicillanic acid, 30 ml. of dichloromethane and 20 ml. of water was added 40% aqueous tetrabutylammonium hydroxide until a pH of 8.0 was obtained. Stirring was continued for 30 minutes at pH 8.0 and then the layers were separated. The aqueous layer was extracted with dichloromethane, and then the combined dichloromethane solutions were dried (Na$_2$SO$_4$) and evaporated in vacuo. This afforded 1.1 g. of the title compound.

The NMR spectrum (in DMSO-d$_6$) showed absorptions at 0.70–1.80 (m, 34H), 2.90–3.50 (m, 8H), 3.93 (s, 1H), 5.10 (s, 2H), 5.23–5.50 (m, 3H), 6.76 (d, 2H), 7.20 (d, 2H), 7.40 (s, 5H), 7.76 (d, 1H) and 8.6 (d, 1H) ppm.

Tetrabutylammonium 6-(2-[4-nitrobenzyloxycarbonylamino]-2-[4-hydroxyphenyl]acetamido)penicillanate is obtained from 6-(2-[4-nitrobenzyloxycarbonylamino]-2-[4-hydroxyphenyl]acetamido)penicillanic acid and tetrabutylammonium hydroxide by the above method.

Tetrabutylammonium 6-[D-(2-benzyloxycarbonylamino-2-phenyl)acetamido]penicillanate, tetrabutylammonium-6-[D-2-(4-nitrobenzyloxycarbonylamino)-2-phenylacetamido]penicillanate and tetrabutylammonium 6-[D-(2-azido-2-phenylacetamido)]-penicillanate are prepared in like manner.

We claim:

1. A compound of the formula:

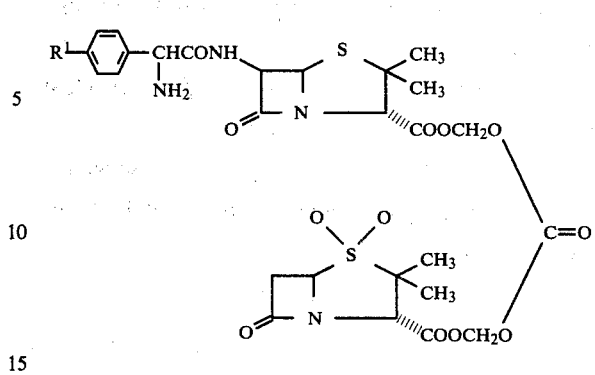

or a pharmaceutically acceptable acid addition salt thereof wherein:

R[1] is hydrogen, hydroxy, formyloxy, alkanoyloxy having from two to seven carbon atoms, alkoxycarbonyloxy having from two to seven carbon atoms or R[2]C$_6$H$_4$COO where R[2] is hydrogen, alkyl having from one to four carbon atoms, alkoxy having from one to four carbon atoms, F, Cl, Br, I or CN.

2. The compound according to claim 1 wherein R[1] is hydrogen.

3. The compound according to claim 1 wherein R[1] is hydroxy.

4. A compound according to claim 1 wherein R[1] is CH$_3$COO, (CH$_3$)$_3$CCOO or (CH$_3$)$_2$CHCOO.

5. A method of treating a bacterial infection in a mammalian subject, which comprises administering thereto an antibacterially effective amount of a compound according to claim 1.

6. A method according to claim 5 wherein in said compound R[1] is hydrogen.

7. A method according to claim 5 wherein in said compound R[1] is hydroxy.

8. A method according to claim 5 wherein in said compound R[1] is CH$_3$COO, (CH$_3$)$_3$CCOO or (CH$_3$)$_2$CHCOO.

9. A pharmaceutical composition, suitable for treating a bacterial infection in a mammalian subject, which comprises an antibacterially effective amount of a compound according to claim 1 and a pharmaceutically acceptable carrier.

10. A compound of the formula:

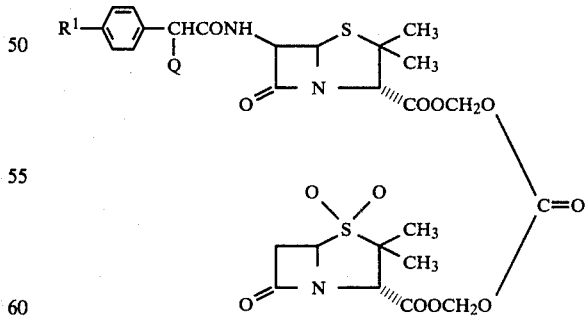

wherein R[1] is hydrogen, hydroxy, formyloxy, alkanoyloxy having from two to seven carbon atoms, alkoxycarbonyloxy having from two to seven carbon atoms or R[2]C$_6$H$_4$COO where R[2] is hydrogen, alkyl having from one to four carbon atoms, alkoxy having from one to four carbon atoms, F, Cl, Br, I or CN; and Q is azido, benzyloxycarbonylamino, 4-nitrobenzyloxycarbonylamino or 1-methyl-2-methoxycarbonyl-vinylamino.

11. A compound according to claim 10 wherein Q is azido and $R^1$ is hydrogen or hydroxy.

12. A compound according to claim 10 wherein Q is 1-methyl-2-methoxycarbonylvinylamino and $R^1$ is hydrogen or hydroxy.

13. A compound of the formula:

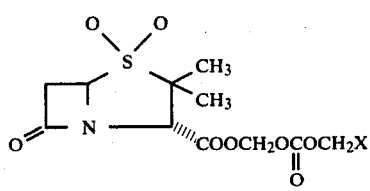

wherein X is Cl, Br or I.

14. The compound according to claim 13 wherein X is I.

15. A compound of the formula:

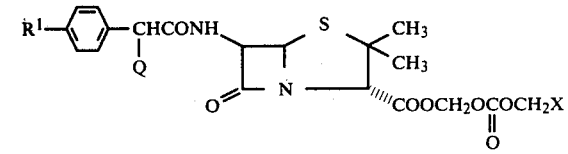

wherein
$R^1$ is hydrogen, hydroxy, formyloxy, alkanoyloxy having from two to seven carbon atoms, alkoxycarbonyloxy having from two to seven carbon atoms or $R^2C_6H_4COO$ where $R^2$ is hydrogen, alkyl having from one to four carbon atoms, alkoxy having from one to four carbon atoms, F, Cl, Br, I or CN;
Q is azido, benzyloxycarbonylamino, 4-nitrobenzyloxycarbonylamino or 1-methyl-2-methoxycarbonylvinylamino; and
X is Cl, Br or I.

16. A compound according to claim 15 wherein $R^1$ is hydrogen or hydroxy and X is I.

17. A compound according to claim 16 wherein $R^1$ is hydroxy.

18. A compound according to claim 16 wherein $R^1$ is hydrogen.

19. The compound according to claim 18 wherein Q is azido.

* * * * *